US009126184B2

(12) United States Patent
Jan et al.

(10) Patent No.: US 9,126,184 B2
(45) Date of Patent: Sep. 8, 2015

(54) DETERGENT ALKYLATION USING A RARE EARTH EXCHANGED CATALYST

(75) Inventors: Deng-Yang Jan, Elk Grove Village, IL (US); Mark G. Riley, Hinsdale, IL (US); Stephen W. Sohn, Arlington Heights, IL (US); Jaime G. Moscoso, Mount Prospect, IL (US); Raelynn M. Miller, LaGrange, IL (US)

(73) Assignee: UOP LLC, Des Plaines, IL (US)

( * ) Notice: Subject to any disclaimer, the term of this patent is extended or adjusted under 35 U.S.C. 154(b) by 896 days.

(21) Appl. No.: 12/639,968

(22) Filed: Dec. 16, 2009

(65) Prior Publication Data

US 2011/0144403 A1    Jun. 16, 2011

(51) Int. Cl.
    *C07C 2/66*    (2006.01)
    *B01J 29/08*   (2006.01)

(52) U.S. Cl.
    CPC ............ *B01J 29/088* (2013.01); *C07C 2/66* (2013.01); *B01J 29/087* (2013.01); *C07C 2529/08* (2013.01)

(58) Field of Classification Search
    CPC .............. C07C 2/54; C07C 2/55; C07C 2/56; C07C 2/57; C07C 2/58; C07C 2/59; C07C 2/60; C07C 2/61; C07C 2/62; C07C 2/63; C07C 2/64; C07C 2/65; C07C 2/66
    USPC .................... 585/467, 49, 449, 455
    See application file for complete search history.

(56) References Cited

U.S. PATENT DOCUMENTS

| | | | |
|---|---|---|---|
| 4,301,317 A | | 11/1981 | Young |
| 4,740,620 A | * | 4/1988 | Dixon et al. ................. 585/446 |
| 5,194,244 A | | 3/1993 | Brownscombe et al. |
| 5,869,021 A | | 2/1999 | Wang et al. |
| 6,133,492 A | | 10/2000 | Anantanenl |
| 6,521,804 B1 | | 2/2003 | Marinangeli et al. |
| 6,756,030 B1 | | 6/2004 | Rohde et al. |
| 6,977,319 B2 | | 12/2005 | Campbell et al. |
| 7,091,390 B2 | | 8/2006 | Jan et al. |
| 7,268,267 B2 | | 9/2007 | Jan et al. |
| 7,297,826 B2 | | 11/2007 | Joly et al. |
| 2003/0211034 A1 | | 11/2003 | Wilson et al. |
| 2005/0203322 A1 | | 9/2005 | Harris |
| 2006/0084567 A1 | | 4/2006 | Kelly et al. |
| 2008/0161621 A1 | * | 7/2008 | Riley et al. .................... 585/468 |
| 2008/0183025 A1 | * | 7/2008 | Van Broekhoven et al. .. 585/722 |

FOREIGN PATENT DOCUMENTS

| | | |
|---|---|---|
| WO | 2007005317 A2 | 1/2007 |
| WO | 2008055121 A2 | 5/2008 |
| WO | WO 2009/071709 A1 | 6/2009 |

OTHER PUBLICATIONS

Thomas B. et al, "Towards a Green Synthesis of LAB's: Effect of Rare Earth Metal Ions on the Benzene Alkylation with 1-Dodecene over NAFAU-Y Zeolites." J. Mater. Sci. vol. 41 (2006) pp. 1611-1616.*

Corma, A., et al.; Comparison of the Information Given by Ammonia t.p.d. and Pyridine Adsorption-Desorption on the Acidity of Dealuminated HY and LaHY Zeolite Cracking Catalysts, Zeolites, Nov. 1987, vol. 7, pp. 559-563.

Ipatieff, V.N. et al.; Reaction Between Benzene and Butadiene in the Presence of Silico-phosphoric Acid Catalyst, Journal American Chem. Soc.; Feb. 28, 1945; vol. 67 (7), pp. 1060-1062.

Proell, W.; The Alkenylation of Aromatics with Butadiene: A Synthesis of 1-Phenyl-2-Butene, Journal of Organic Chemistry, vol. 16 (2), Feb. 1951, pp. 178-184.

U.S. Appl. No. 12/639,973, filed Dec. 16, 2009, Riley et al.
U.S. Appl. No. 12/639,971, filed Dec. 16, 2009, Riley et al.
U.S. Appl. No. 12/639,596, filed Dec. 16, 2009, Jan et al.

Gee et al., A Kinetic and mechanistic study of the double bond and skeletal isomerization of 1-tetradecene on SAPO-11, Applied Catalysis A: General 360 , 71-80, (2009).

Peterson et al., Hydroisomerization of Normal Olefins under Alkylation Conditions, I&EC Product & Research Dev., 4, No. 4, 261-265 (1965).

Venuto et al., Organic Reactions Catalyzed by Crystalline Aluminosilicates, Journal of Catalysis, 5, 81-98, 87 (1966).

Deshumkh et al., Alkylation of benzene with long chain (C8-C18) linear primary alcohols over zeolite-Y, Catalysis Letters 64, 247-250 (2000).

Galinski, et al., Alkylation of benzene by α-olefins on modified faujasite, Petroleum Chemistry vol. 35, 2, pp. 143-146 (1995).

He et al., Liquid phase alkylation of benzene with propylene over large pore zeolite catalysts, Jour. of Fuel Chem & Tech. 27(3) p. 203-208, Chinese (English Abstract ), (1999).

Meriaudeau et al., Zeolite based catalysts for linear alkylbenzene production: Institut de Recherches, Elsevier Catalysis Today 38, p. 243-247 (1997).

Minachev et al., New Application of Zeolite Systems in Catalitic Organic Syntheses, Inst. of Organic Chem., Moscow, 1989 Elsevier Science, p. 47 (1989).

Sivasanker et al., Shape Selective Alkylation of Benzene with Long Chain Alkenes over Zeolites, 10th Intl Congress of Catalysis, Budapest, Hungary (1992).

(Continued)

*Primary Examiner* — In Suk Bullock
*Assistant Examiner* — Sharon Pregler

(57) ABSTRACT

A process is disclosed using a new catalyst for use in the alkylation of benzene with a substantially linear olefin. The catalyst allows for cation exchange with a rare earth element to increase the alkylation of benzene, while reducing the amount of isomerization of the alkyl group. This is important for increasing the quality of the alkylbenzene by increasing the linearity of the alkylbenzene.

15 Claims, 1 Drawing Sheet

(56) References Cited

OTHER PUBLICATIONS

Thomas et al., Towards a Green Synthesis of LAB's: Effect of Rare Earth Metal Ions on the Benzene Alkylation . . . , Journal of Mater Sci 41, p. 1611-1616, (2006).
Thomas et al., Alkylation of Benzene with 1-octene over rare earth exchanged HFAU-Y Zeolites, Reaction Kinetics and Cat. Ltrs, V85, 1, p. 29-36 (2005).
Kovacheva et al., Oxidative methylation of toluene with methane using X zeolite catalyst . . . , Applied Catalysis A: General 223, p. 121-128 (2002).
Madhavi et al., Side-Chain Alkylation of Heterocyclic Compounds over Modified Zeolites, Studies in Surface Science & Cat. v 154, p. 2760-66 (2004).
Ono et al., Selective reactions over solid base catalysts, Tokyo, Japan, Catalysis Today, 38 p. 321-337 (1997).
Wang, Lee, Cai, Park., Benzene alkylation with 1-dodecene over H-mordenite zeolite, Catalysis Letters, V 76, No. 1-2, (2001).
Yu, Sidorenko, Galich, Selective Alylation of Methyl-Substituted Aromatic Hydrocarbons on Acid and Basic Zeolites, Petrol. Chem V31, p. 57-69 (1991).
Vasil'ev et al., Catalysts of obtaining styrene and its derivatives, Khimiya i Teknologiya Topliv I Masel—1997_MT_Eng (in Russian).
Vasil'ev et al., Catalysts of obtaining styrene and its derivatives, Khimiya i Teknologiya Topliv I Masel—1997_MT_Eng (in English).
Wieland et al., Side-Chain Alkylation of Toluene with Methanol over Alkali-Exchanged Zeolites X, Y, L, and β, Jour. of Catalysis, 173, 490-500 (1998).
Zeng, Study on a New Technology of p-Nitrobenzoic Acid Production, Shiyou Huagong Petro. Technology (1999), Chinese with English Abstract.
PCT International Search Report and Written Opinion; Date of mailing: Apr. 28, 2011; PCT/US2010/046402.
European Search Report dated Mar. 31, 2014 for Application No./ Patent No. 10842388.0.

\* cited by examiner

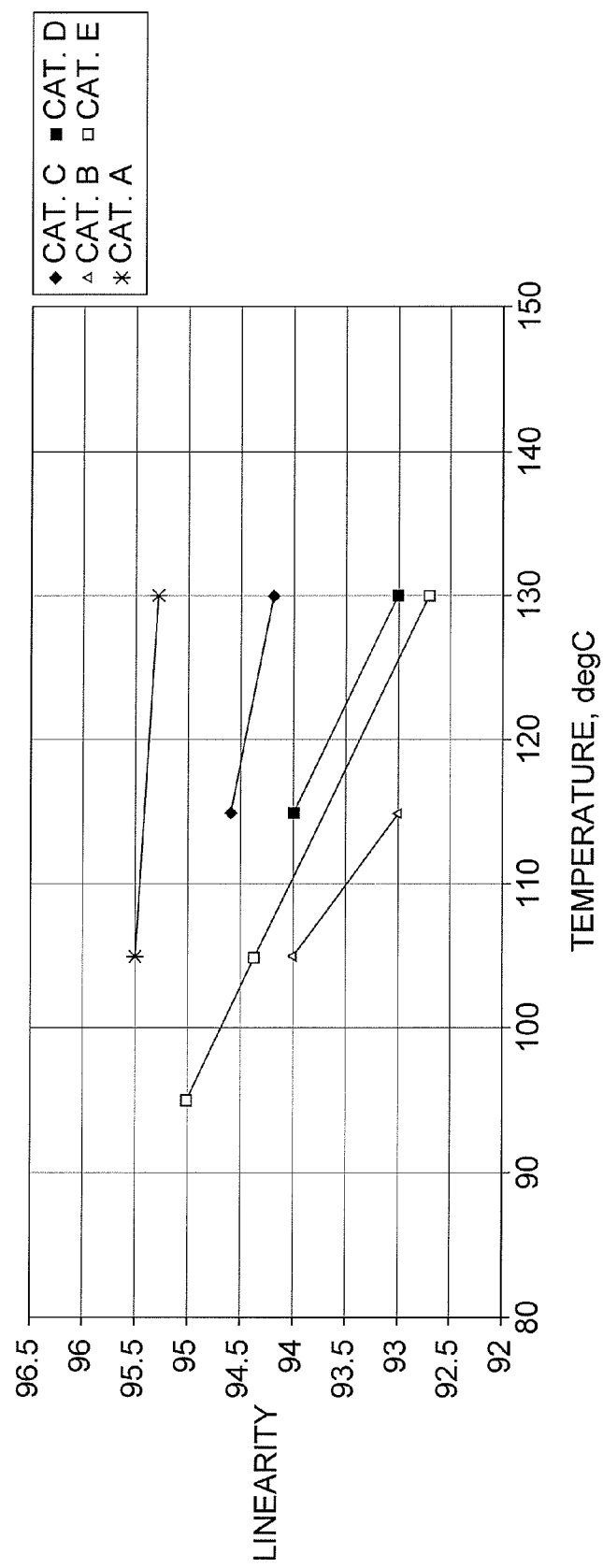

US 9,126,184 B2

DETERGENT ALKYLATION USING A RARE EARTH EXCHANGED CATALYST

FIELD OF THE INVENTION

The present invention is directed to highly selective, modified catalysts and the process of using the catalysts. The catalysts are for use in the alkylation of aromatic compounds.

BACKGROUND OF THE INVENTION

Alkylation of benzene produces alkylbenzenes that may find various commercial uses, e.g., alkylbenzenes can be sulfonated to produce surfactants, for use in detergents. In the alkylation process, benzene is reacted with an olefin the desired length to produce the sought alkylbenzene. The alkylation conditions comprise the presence of homogeneous or heterogeneous alkylation catalyst such as aluminum chloride, hydrogen fluoride, or zeolitic catalysts and elevated temperature.

Various processes have been proposed to alkylate benzene. One commercial process involves the use of hydrogen fluoride as the alkylation catalyst. The use and handling of hydrogen fluoride does provide operational concerns due to its toxicity, corrosiveness and waste disposal needs. Solid catalytic processes have been developed that obviate the need to use hydrogen fluoride. Improvements in these solid catalytic processes are sought to further enhance their attractiveness through reducing energy costs and improving selectivity of conversion while still providing an alkylbenzene of a quality acceptable for downstream use such as sulfonation to make surfactants.

Alkylbenzenes, to be desirable for making sulfonated surfactants must be capable of providing a sulfonated product of suitable clarity, biodegradability and efficacy. With respect to efficacy, alkylbenzenes having higher 2-phenyl contents are desired as they tend, when sulfonated, to provide surfactants having better solubility and detergency. Thus, alkylbenzenes having a 2-phenyl isomer content in the range from about 25 to about 35 percent are particularly desired.

Improvements in the catalysts have facilitated the production of linear alkylbenzenes, as shown in U.S. Pat. No. 6,133,492, U.S. Pat. No. 6,521,804, U.S. Pat. No. 6,977,319, and U.S. Pat. No. 6,756,030. However, problems exist with many existing catalysts, and a better understanding, can lead to further improvements in the catalysts.

SUMMARY OF THE INVENTION

The present invention provides for a process for producing a monoalkylated aromatic compound having an increased linearity of the alkyl group. The process comprises reacting an aromatic feedstock with an olefinic compound in an alkylation reactor at reaction conditions using a catalyst, where the catalyst has a rare earth element incorporated into the zeolitic framework. The catalyst has a silica to alumina ratio of less than 8, and the rare earth element is exchanged to a degree such that the molar ratio of rare earth element to aluminum is between 0.17 and 0.4. When taking valance charge into account, the ratio is between 0.51 and 1.2, with the balance being alkali, alkaline earth, ammonium cations or a mixture thereof.

In one embodiment, the process includes adding water to the feed to the reactor. The water is added in an amount to keep the water below 1000 ppm by weight of the total feed to the reactor. The process is operated at conditions to keep the reactants in the liquid phase.

Other objects, advantages and applications of the present invention will become apparent to those skilled in the art from the following drawings and detailed description.

BRIEF DESCRIPTION OF THE DRAWING

FIG. 1 shows the linearity of catalysts that have retained some alkali cations.

DETAILED DESCRIPTION OF THE INVENTION

Catalysts are strongly affected by materials that either combine with the catalyst, or can in one form or another reduce the catalytic activity of the catalyst. These materials are poisons to the catalyst, and include materials such as alkali metals, alkaline earth metals, ammonia, amine and their ions. These poisons are typical, and lead to pretreatments of feeds to catalytic reactors to protect the catalyst, by removing any poisons in the process stream. As shown by Venuto, P. B., et al., *J. of Catal.*, 4, 81-98, 87 (1966), "[l]ow sodium levels were critical for high alkylation activity with REX catalyst." As the sodium level was increased from 0.22 wt. % to 0.79 wt. %, the activity decreased to almost half.

The alkylation of aromatics with olefins in important for several commercially important technologies. Ethyl benzene (EB), cumene (isopropyl benzene), and larger chained alkylbenzenes (detergents) are the three most economically important examples. The detergents preferably made using longer chained linear alkyl groups, such as C8 to C13, to form linear alkyl benzenes. These alkylation reactions are carried out using acid catalysts, either homogeneous catalysts such as HF, or heterogeneous catalyst such as $AlCl_3$, silica-alumina, and zeolites. Although these are all acid catalyzed processes, there are enough differences that they are all practiced with different catalysts. Skeletal isomerization is an example of a concern in the LAB process, and which makes the use of catalysts suitable for EB or cumene of less value in the LAB process.

The production of linear alkylbenzenes has traditionally been made in two commercial forms, low 2-phenyl and high 2-phenyl. Low 2-phenyl LAB is made by HF alkylation and results in a 2-phenyl concentration between 15 and 20 mass percent of the LAB. This is due to the homogeneous acid, HF, lack of preference for catalyzing the attachment of the benzene to the olefin chain. There is not alkylation on the terminal carbons, and the internal carbons have a nearly equal probability of alkylation, and which produces shorter chained alkyl groups extending from the benzene. High 2-phenyl LAB has historically been made using $AlCl_3$ alkylation and results in a 2-phenyl concentration between 30 and 35 mass percent of the LAB. While it is possible to produce LAB with different 2-phenyl contents, there is no market for these products, and consequently the efforts have been to replace these environmentally unfriendly catalysts.

In 1995, UOP and Cepsa introduced a detergent alkylation process using the first environmentally friendly solid bed alkylation process for the production of LAB. The catalyst was a fluorided silica-alumina catalyst, and the process produces a high 2-phenyl LAB product. This process has nearly completely replaces the use of $AlCl_3$ in detergent alkylation. However, it uses considerably more energy than the HF process due to the much higher benzene to olefin ratio in the process, and produces slightly more dialkylate than the HF process.

While ethylbenzene, cumene and LAB are all produced in processes using acid catalysts, there are a number of key features that differentiate LAB from either ethylbenzene or cumene. One is the length of the olefin and the reactions that the olefin can undergo. Solid acid catalysts are know to catalyze both double bond isomerization and skeletal isomerization in linear olefins. Most studies of double bond and skeletal isomerization of linear olefins has focused on 1-butene. This is due to the desire to make isobutene for MTBE, an oxygenate for gasoline, or polyisobutene. Gee and Prampin, *Applied Catalysis A: General* 360 (2009), 71-80. Even a week acid catalyst, like SAPO-11, produces skeletal isomerization, and is easily observed at 142 C, and that skeletal isomerization is temperature dependent.

It is known that skeletal isomerization of linear olefins occurs in the production of LAB over solid acid catalysts. In 1965, in an article titled "Hydroisomerization of Normal Olefins Under Alkylation Conditions" showed that skeletal isomerization was favored by high acid concentrations and high temperatures (Peterson, A. H.; Phillips, B. L.; and Kelly, J. T.; *I&EC*, 4, No. 4, 261-265, 1965). Also, as shown in U.S. Pat. No. 4,301,317 to Young, Table 2, in the reference, compares the amount of linear phenyldodecane produced by alkylation of 1-dodecene with benzene over eight different zeolites. All of the zeolites exhibited skeletal isomerization. Inhibiting skeletal isomerization is an important challenge to be addressed, if one is to produce highly linear detergent range alkylbenzenes. It is further worth noting that Beta zeolite, which is commonly used in the production of ethylbenzene and cumene is unsuitable for detergent range LAB production due to its tendency to skeletally isomerizes the linear olefins prior to their alkylation. Because ethylene and propylene only have one isomer, both the double bond and skeletal isomerization of the catalyst are moot and for this reason one cannot predict that a process or catalyst for ethylbenzene or cumene production will necessarily extend to LAB.

A second difference between alkylation of long chain linear olefins with benzene differs from that of ethylbenzene or cumene is the number of products. Ethylbenzene and cumene are unique chemical compounds whereas LAB is a mixture of compounds that results from the fact that long chain linear olefins have multiple positions for the benzene to insert itself. As can be seen from Young's data in U.S. Pat. No. 4,301,317, molecular sieves can reduce or prohibit the formation of some phenylalkane isomers. This is phenomena is called shape selectivity and occurs because the molecular sieve doesn't possess enough space for the molecule to be formed. Since the commercially desirable detergent range linear alkylbenzenes, "low 2-phenyl LAB" and "high 2-phenyl LAB" have relative narrow windows on their 2-phenylalkane content, an acidic molecular sieve catalyst that has good characteristics for producing ethylbenzene or cumene cannot be assumed to be appropriate for producing commercially acceptable detergent range LAB.

A third way in which the alkylation of long chain linear olefins with benzene differs from that of ethylbenzene or cumene is in the impact of the benzene to olefin ratio. Alkylation processes to convert ethylene to ethylbenzene and propylene to cumene operate at significantly low benzene to olefin ratios than solid detergent alkylation processes. It has long been known that monoalkylate selectivity can be maximized by operating at high benzene to olefin ratios. High benzene to olefin ratios also means the ratio of benzene to monoalkylate is high and the higher the weight fraction of benzene relative to other aromatics, the higher the yield of monoalkylate. In the production of ethylbenzene or cumene low benzene to olefin ratios can be employed to minimize energy usage because the polyethylbenzene or polypropylbenzene can be easily transalkylated with benzene to produce the desired product, ethylbenzene or cumene. In the detergent alkylation process, where a solid fluorided amorphous silica-alumina catalyst is employed, shape selectivity does not come into play due to the very large pores and the only way to control the amount of dialkylbenzene is to use high benzene to olefin ratios. Converting long chain linear dialkylbenzenes back to long chain linear monoalkylbenzenes can be done, but with significantly lower efficiency than for ethylbenzene or cumene. Some of the transalkylation occurs though dealkylation followed by alkylation with benzene. When transalkylation occurs through this pathway some of the olefin undergoes skeletal isomerization, which lowers overall product linearity.

Low benzene to olefin ratios also promotes the skeletal isomerization of linear olefins. Because skeletal isomerization is a monomolecular reaction and alkylation is a bimolecular reaction, lowering the benzene to olefin ratio effectively increases the olefin concentration which causes the rate of olefin skeletal isomerization to increase faster than the rate of olefin alkylation. Thus, in solid detergent alkylation processes, one is faced with the choice of operating at high benzene to olefin ratios and accepting the high energy cost or finding catalysts with the appropriate acidity such that skeletal isomerization of the linear olefins is minimal.

It has been found that incorporating some rare earth elements into a zeolite supercage, the efficiency is increased in producing a primary alkylation product. The means to achieve an increasing amount of rare earth into the structure is by using a lower ratio Faujasite and a designed rare earth incorporation technique. By low ratio, it is meant to indicate the silica to alumina ratio.

The incorporation of rare earth exchanged low ratio zeolite reduces the geometric space in the supercage, and it also reduces acidity due to an increase in the number of framework aluminum at the low ratios. The reduced space and acidity significantly suppresses the isomerization and cracking pathways, while the primary alkylation pathway is not affected. This increases product by decreasing the undesired side reactions that occur. One of the benefits from the new catalyst is a high linearity of the alkylbenzene for use in detergent alkylation. Contrary to what one would expect, it was found that incorporating or leaving some alkali or alkaline earth cations in the catalyst significantly improves catalyst performance. And especially in the performance around the linearity of the alkylbenzene, and the retention of linearity at increased operating temperatures. The present invention is aimed at producing a product having a linearity of at least 90%.

The present invention comprises a new catalyst for alkylation of aromatics comprising a zeolite having a silica to alumina molar ratio of less than 8, and a rare earth element incorporated into the zeolitic framework. The silica to alumina molar ratio is preferably less than 6 and more preferably less than 5.6. The catalyst can be a low silica to alumina molar ratio Y type zeolite, X type zeolite, or a zeolite have EMT/FAU intergrowth.

The catalyst is formed by using a Y zeolite or X zeolite and modified with an alkali or alkaline earth element or nitrogen compound, such as sodium, barium, ammonia or amine to control the acidity. The catalyst is then ion exchanged with a rare earth element to remove a portion of the alkali or alkaline earth elements, and to provide for larger ions in the zeolites cages. The catalyst can be in extruded or bead form. The catalyst can be prepared by first exchanging the zeolite powder with a rare earth element and then forming the zeolite into pellets or beads. An alternative is to form the zeolite into pellets or beads and then perform the rare earth exchange.

When the catalyst is a Y type zeolite, the silica to alumina molar ratio is between 2.8 and 8, and preferably between 3 and 6, and when the catalyst is an X type zeolite, the silica to alumina molar ratio is between 2 and 2.8.

The catalyst includes a rare earth element that is incorporated into the supercages of the zeolite to provide some steric restraint. The supercages are large cavities, relative to the pores, in the zeolites that usually have a diameter greater than 1 nm. The supercages are sometimes cavities formed with the intersection of different pores in the zeolite. This is a region where there is less steric hindrance for some catalytic reactions when compared with the pores. This limits undesirable side reactions. Rare earth elements that can be used include at least one of the following: scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thullium (Tm), ytterbium (Yb), and lutetium (Lu). Preferred rare earth elements include at least one of yttrium (Y), lanthanum (La), cerium (Ce), praseodymium (Pr), neodymium (Nd), gadolinium (Gd), dysprosium (Dy), erbium (Er), and ytterbium (Yb).

The rare earth element is cation exchanged with the zeolite sufficient to where the rare earth element to aluminum molar ratio is between 0.51 and 1.2. The catalyst is further cation exchanged with an alkali, an alkaline earth element, or nitrogen compound cation.

The catalyst can further include a binder wherein the binder comprises alumina, silica, magnesium silicates, zirconia, and mixtures thereof. The binder can also comprise natural or synthetic clays, which are made up of various metal oxides. The binder provides hardness to the catalyst to improve the physical durability of the catalyst from abrasion during operation.

In one embodiment, the catalyst is an X type zeolite having an alumina molar ratio less than 2.8. A rare earth element is incorporated into the zeolitic framework. The rare earth elements include yttrium (Y), lanthanum (La), cerium (Ce), praseodymium (Pr), neodymium (Nd), europium (Eu), gadolinium (Gd), terbium (Tb), dysprosium (Dy), holmium (Ho), erbium (Er), thullium (Tm), ytterbium (Yb), and lutetium (Lu). Preferred rare earth elements include yttrium (Y), lanthanum (La), cerium (Ce), praseodymium (Pr), neodymium (Nd), gadolinium (Gd), dysprosium (Dy), erbium (Er) and ytterbium (Yb). The rare earth elements contribute to developing steric hindrance within the zeolite pores, and modifying the acidity of the X type zeolite, to reduce the acidity from strong to moderate. It is preferred that the silica to alumina molar ratio is less than 2.8, and more preferably less than 2.5, with a most preferred ratio between 1 and 2.4.

The catalyst has the rare earth elements exchanged to a degree that the molar ratio of rare earth elements to aluminum in the catalyst is in the range between 0.51 and 1.2. A balance of the cation exchange to control the acidity is with alkali or alkaline earth elements.

In the detergent alkylation process, the retention of linearity of the alkyl group is important for the quality of the detergents produced from alkylaromatics. It was found that the incorporation of some alkali, or alkaline earth, elements on the catalyst improved the catalyst performance with respect to retaining linearity of the alkyl group without affecting the activity adversely. The results of alkylation tests with the rare earth exchanged catalyst show the high degree of linearity of the product over a wide range of operating temperatures in FIG. 1.

The process for producing a monoalkylated aromatic compound comprises: passing an aromatic feedstock and an olefinic compound to an alkylation reactor. The alkylation reactor has an alkylation catalyst comprising a zeolite having a silica to alumina molar ratio less than 8 and includes a rare earth element incorporated into the zeolitic framework. The reactor generates an effluent stream comprising the monoalkylated aromatic compound, and is passed to a separation unit. The separation unit recovers the monoalkylated aromatic compound, and generates an aromatic stream and a non-product alkylated aromatic stream. The non-product alkylated aromatic stream generally comprises dialkylated aromatic compounds and can be passed to a transalkylation reactor to improve the product yield.

Aromatic compounds and olefins are reacted under alkylation conditions in the presence of a solid alkylation catalyst. The alkylation conditions generally include a temperature in the range between about 80° C. and about 200° C., most usually at a temperature not exceeding about 175° C., e.g., 100° C. to 160° C. Typically, as the catalyst ages, the temperature of the alkylation is increased to maintain desired activity. The alkylation is an exothermic reaction and thus in a substantially adiabatic reactor, the effluent is at a higher temperature than that of the feed. A substantially adiabatic reactor is one where the increase in temperature of the effluent over that of the feed accounts for at least about 75 percent of heat generated by the reactions in the reaction zone. The preferred aromatic compound is benzene, and the preferred olefins are linear alpha olefins having from 8 to 20 carbon atoms. During the alkylation process, the catalyst deactivates, and the temperature is allowed to increase to compensate for catalyst deactivation. With deactivation, and with increases in temperature, product linearity is reduced. This catalyst minimizes the changes in the product linearity over the life of the catalyst and extends the useful life of the catalyst, by maintaining a higher product linearity during the process, such that with increasing temperature, there is still a high degree of linearity maintained over prior catalysts.

The temperature within a reaction zone is maintained within a suitable range by providing a large excess of aromatic compound to the reaction zone to absorb heat. Where the aliphatic feedstock contains paraffins, the paraffins also serve to absorb heat from the exothermic reactions. High exothermic temperatures during the alkylation can result in untoward effects in terms of not only catalyst deactivation but also in product quality degradation, especially skeletal isomerization, and, in particular, skeletal isomerization of the olefin.

The alkylation reactor is generally a fixed bed type reactor, where the reactants flow over the catalyst as the reactants flow through the reactor. The catalyst can be regenerated in the alkylation reactor to remove carbon deposits by taking the reactor off-line.

The alkylation reactor can also comprise a plurality of reactors with intercoolers between the reactors to remove heat and maintain the operation in a desirable temperature range.

In one embodiment, the catalyst in the present alkylation reaction process is an X type zeolite having a silica to alumina molar ratio less than 2.8, and the zeolite includes a rare earth element incorporated into the zeolitic framework. The rare earth elements include at least one from the group comprising: yttrium (Y), lanthanum (La), cerium (Ce), praseodymium (Pr), neodymium (Nd), europium (Eu), gadolinium (Gd), terbium (Tb), dysprosium (Dy), holmium (Ho), erbium (Er), thullium (Tm), ytterbium (Yb), and lutetium (Lu).

The alkylation process with the new catalyst also can include the addition of water to the alkylation reactor. The water in the reactor adsorbs onto the catalyst during the reaction, and comprises between 0.5 and 6 weight percent of the total catalyst weight. A preferred amount of water adsorbed onto the catalyst comprises between 1 and 3 weight percent of the total catalyst weight. The amount of water is low and kept to below 1000 ppm by weight of the combined feed of aromatic compound and olefin to the alkylation reactor. Preferably, the amount of water is less than 900 ppm by weight of the combined feed to the reactor.

The alkylation process for detergent alkylation is preferably operated in the liquid phase. To maintain the reactants in the liquid phase, the reactor is operated at a pressure between 1300 and 7000 kPa, with a preferred operating pressure between 2500 and 4500 kPa.

In an alternate embodiment, the process of benzene alkylation comprises passing an aromatic feedstock and an olefinic compound to an alkylation reactor. The alkylation reactor has an alkylation catalyst comprising a Y or X type zeolite having greater than 16.5 wt % of rare earth in the zeolite with the balance being alkali, alkaline earth element, or nitrogen compound cations incorporated into the zeolitic framework. The choice of rare earth elements is as stated above. In the preferred operation the catalyst has a silica to alumina molar ratio between 3 and 6.

Experiments were performed where catalyst A is the catalyst of the present invention and catalysts B, C, D and E were prepared for comparative purposes. Catalyst A was prepared by rare earth exchange of Y-54 of 0.3 M of rare earth solution made up from rare earth stock solution obtained from Moly Corp. at 75-80° C. for 2 hours. The exchange utilizes 1.0 gm of rare earth solution per gram of Y-54 powder on an as received basis. At the end of the rare earth exchange, the slurry is filtered under vacuum and the resulting filter cake is washed with 10 grams of de-ionized water per gram of powder. The filter cake is dried and then steamed at 550° C. at 50% steam for 1.5 hours. The steamed rare earth exchanged powder is exchanged with a second rare earth solution and water wash following the same procedure as above. The powder is formulated into a catalyst of cylindrical pellets with 1/16" (0.16 cm) diameter consisting of 80 wt % zeolite and 20 wt % binder on a volatile free basis.

Catalysts B, C, D and E are prepared following the same procedure used for preparing catalyst A, with the exception that no second rare earth exchange is performed. Instead, an ammonium exchange step of various degrees is performed following the steaming step to yield a final powder of different rare earth and sodium contents. The ammonium exchange is typically done at 70° C. for 1 to 2 hours using a 10 wt % $NH_4NO_3$ solution.

TABLE

Catalyst Property and Sensitivity of Product Linearity to Temperatures

| Catalyst | C | D | B | E | A |
|---|---|---|---|---|---|
| Si | 29.3 | 30.3 | 30.7 | 29 | 26.3 |
| Al | 10.7 | 11 | 10.7 | 10.8 | 9.9 |
| Na | 0.16 | 0.19 | 0.058 | 0.22 | 0.55 |
| Ce | 1.51 | 1.64 | 1.48 | 1.95 | 2.72 |
| La | 8 | 7.7 | 7.1 | 7.4 | 10.3 |
| Pr | 1.02 | 0.9 | 0.84 | 0.98 | 1.38 |
| Nd | 2.44 | 2.1 | 2 | 2.25 | 3.25 |
| Si/Al | 2.641 | 2.656 | 2.767 | 2.589 | 2.562 |
| RE/Al | 0.70 | 0.65 | 0.62 | 0.67 | 1.03 |
| wt % RE | 12.97 | 12.34 | 11.42 | 12.58 | 17.65 |
| product linearity response to temperature, % deg C.$^{-1}$ | — | −0.0677 | −0.1 | −0.0662 | −0.008 |

The catalyst is tested in a plug flow reactor operating at inlet temperatures from 95 to 130° C. The test condition includes a benzene to olefin molar ratio of the feed of about 30, a pressure of 500 psig, and catalyst LHSV is 3.75 $hr^{-1}$. The reaction is carried out in liquid phase condition. The olefin conversions are 100% or close to 100% with the calculations based on the Bromine Index in the feed and the product. The composition of the product is analyzed by gas chromatography. The product linearity is summarized in FIG. 1. The sensitivity of product linearity to temperature is shown in FIG. 1 and reported also in the Table along with the zeolite properties. The data show that product linearity and the sensitivity of product linearity to temperatures are a function of rare earth and sodium contents. As shown in the Table, Catalyst A contains greater than 16.5 wt % rare earth and has higher sodium content. It shows higher product linearity, which is not sensitive to temperature changes. Conceivably, the catalyst is capable of operating over a wide range of temperatures without incurring changes in product linearity. Furthermore, as the catalyst deactivates with time, the operating temperature needs to be adjusted upward to compensate for the activity degradation. Catalyst A can achieve the goal of maintaining the activity via raising the operating temperature without sacrificing the product linearity.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for producing a monoalkylated aromatic compound comprising:
    passing a non-basic aromatic feedstock and an olefinic compound to an alkylation reactor, wherein the alkylation reactor comprises a catalyst comprising a zeolite having a silica to alumina molar ratio less than 8 and a rare earth element incorporated into the zeolitic framework, wherein the rare earth element is in an amount greater than 16.5 wt % of the zeolite with the balance being alkali, alkaline earth, nitrogen compound cations, or a mixture thereof, thereby generating an effluent stream, and wherein the rare earth elements are exchanged to a degree that the rare earth to aluminum molar ratio is in the range from 0.51 to 1.2, and wherein the balance of cation exchange is selected from the group consisting of alkali, alkaline earth, nitrogen compound cations, and mixtures thereof, and wherein the amount of alkali, alkaline earth, or nitrogen compound cations are substituted to the extent that the ratio of the alkali, alkaline earth, or nitrogen compound to aluminum is greater than 0.05;
    passing the effluent stream to a separation process thereby generating an aromatic stream, a product stream comprising a monoalkylated aromatic compound, and a non-product alkylated aromatic stream.

2. The process of claim 1 further comprising adding water to the alkylation reactor.

3. The process of claim 2 wherein the water is added in an amount to keep the water concentration below 1000 ppm by weight of the combined feed to the alkylation reactor.

4. The process of claim 3 wherein the water is added in an amount to keep the water concentration below 900 ppm by weight of the combined feed to the alkylation reactor.

5. The process of claim 1 further comprising adding water to the alkylation reactor where the water adsorbs on the catalyst and comprises between 0.5 and 6 wt. % of the catalyst.

6. The process of claim 1 wherein the catalyst comprises:
    an X type zeolite having a silica to alumina molar ratio less than 2.8; and a rare earth element incorporated into the zeolitic framework wherein the rare earth element is selected from the group consisting of yttrium (Y), lanthanum (La), cerium (Ce), praseodymium (Pr), neodymium (Nd), europium (Eu), gadolinium (Gd), terbium (Tb), dysprosium (Dy), holmium (Ho), erbium (Er), thullium (Tm), ytterbium (Yb), lutetium (Lu), and mixtures thereof.

7. The process of claim 6 wherein the catalyst has at least one rare earth element selected from the group consisting of yttrium (Y), lanthanum (La), cerium (Ce), praseodymium (Pr), neodymium (Nd), gadolinium (Gd), dysprosium (Dy), erbium (Er), ytterbium (Yb), and mixtures thereof.

8. The process of claim 6 wherein the rare earth elements in the catalysts are exchanged to a degree that the rare earth to aluminum molar ratio is in the range from 0.51 to 1.2 with the balance being alkali, alkaline earth element, nitrogen compound cations, or a mixture thereof.

9. The process of claim 1 wherein the alkylation reactor is operated at a temperature between 80° C. and about 200° C.

10. The process of claim 9 wherein the alkylation reactor is operated at a temperature between 100° C. to 160° C.

11. The process of claim 1 wherein the alkylation reactor is operated at a pressure between 1300 to 7000 kPa.

12. The process of claim 11 wherein the alkylation reactor is operated at a pressure between about 2500 and 4500 kPa.

13. The process of claim 1 wherein the catalyst comprises:
   a low ratio Y type zeolite having a silica to alumina molar ratio less than 8; and
   a rare earth element incorporated into the zeolitic framework wherein the rare earth element is selected from the group consisting of yttrium (Y), lanthanum (La), cerium (Ce), praseodymium (Pr), neodymium (Nd), europium (Eu), gadolinium (Gd), terbium (Tb), dysprosium (Dy), holmium (Ho), erbium (Er), thullium (Tm), ytterbium (Yb), lutetium (Lu), and mixtures thereof.

14. The process of claim 13 wherein the zeolite is a Y type zeolite with a silica to alumina molar ratio between 3 and 8.

15. The process of claim 13 wherein the rare earth elements are selected from the group consisting of yttrium (Y), lanthanum (La), cerium (Ce), praseodymium (Pr), neodymium (Nd), gadolinium (Gd), dysprosium (Dy), erbium (Er), ytterbium (Yb), and mixtures thereof.

\* \* \* \* \*